(12) United States Patent
Hayashi et al.

(10) Patent No.: US 7,403,278 B2
(45) Date of Patent: Jul. 22, 2008

(54) SURFACE INSPECTION APPARATUS AND SURFACE INSPECTION METHOD

(75) Inventors: Yoshinori Hayashi, Kanagawa-ken (JP); Hiroyuki Naraidate, Iwate-ken (JP); Makoto Kyoya, Kanagawa-ken (JP); Koji Izunome, Niigata-ken (JP); Hiromi Nagahama, Niigata-ken (JP); Miyuki Shimizu, Niigaa Prefecture (JP); Kazuhiko Hamatani, Kanagawa-ken (JP)

(73) Assignees: Shibaura Mechatronics Corporation, Kanagawa (JP); Covalent Materials Corporation, Tokyo (JP)

( * ) Notice: Subject to any disclaimer, the term of this patent is extended or adjusted under 35 U.S.C. 154(b) by 0 days.

(21) Appl. No.: 11/754,417

(22) Filed: May 29, 2007

(65) Prior Publication Data

US 2007/0222977 A1 Sep. 27, 2007

Related U.S. Application Data

(63) Continuation of application No. PCT/JP2005/021997, filed on Nov. 30, 2005.

(30) Foreign Application Priority Data

Nov. 30, 2004 (JP) ............................. 2004-345141

(51) Int. Cl.
*G01B 21/00* (2006.01)
(52) U.S. Cl. ............... 356/237.1; 356/237.2; 356/237.5
(58) Field of Classification Search .... 356/237.1–237.5
See application file for complete search history.

(56) References Cited

U.S. PATENT DOCUMENTS

| | | | | | |
|---|---|---|---|---|---|
| 6,147,357 | A | * | 11/2000 | Nicolesco | 250/559.46 |
| 6,262,432 | B1 | * | 7/2001 | Brunfeld et al. | 250/559.45 |
| 6,294,793 | B1 | * | 9/2001 | Brunfeld et al. | 250/559.45 |
| 7,280,197 | B1 | * | 10/2007 | Rosengaus | 356/237.1 |
| 2003/0184743 | A1 | * | 10/2003 | Hiramoto et al. | 356/237.1 |
| 2005/0024632 | A1 | * | 2/2005 | Plemmons et al. | 356/237.1 |
| 2005/0062960 | A1 | * | 3/2005 | Tsuji et al. | 356/237.2 |

FOREIGN PATENT DOCUMENTS

| | | |
|---|---|---|
| JP | 8029146 | 2/1996 |
| JP | 11-201906 | 7/1999 |
| JP | 2003-139523 | 5/2003 |
| JP | 2003-243465 | 8/2003 |

* cited by examiner

*Primary Examiner*—Michael P Stafira
(74) *Attorney, Agent, or Firm*—Volpe and Koenig P.C.

(57) ABSTRACT

A surface inspection apparatus, for inspecting a plurality of surfaces formed in a peripheral edge portion of a plate-like object, includes a image pickup mechanism, which photographs the peripheral edge portion of the plate-like object having a plurality of surfaces, and an image processing device, which processes an image obtained by the photographing device. The image pickup mechanism includes an optical system which guides images of the plurality of surfaces of the plate-like object in one direction, and a camera unit having an image pickup surface, on which the images of the plurality of surfaces guided by the optical system in the one direction are formed.

6 Claims, 6 Drawing Sheets

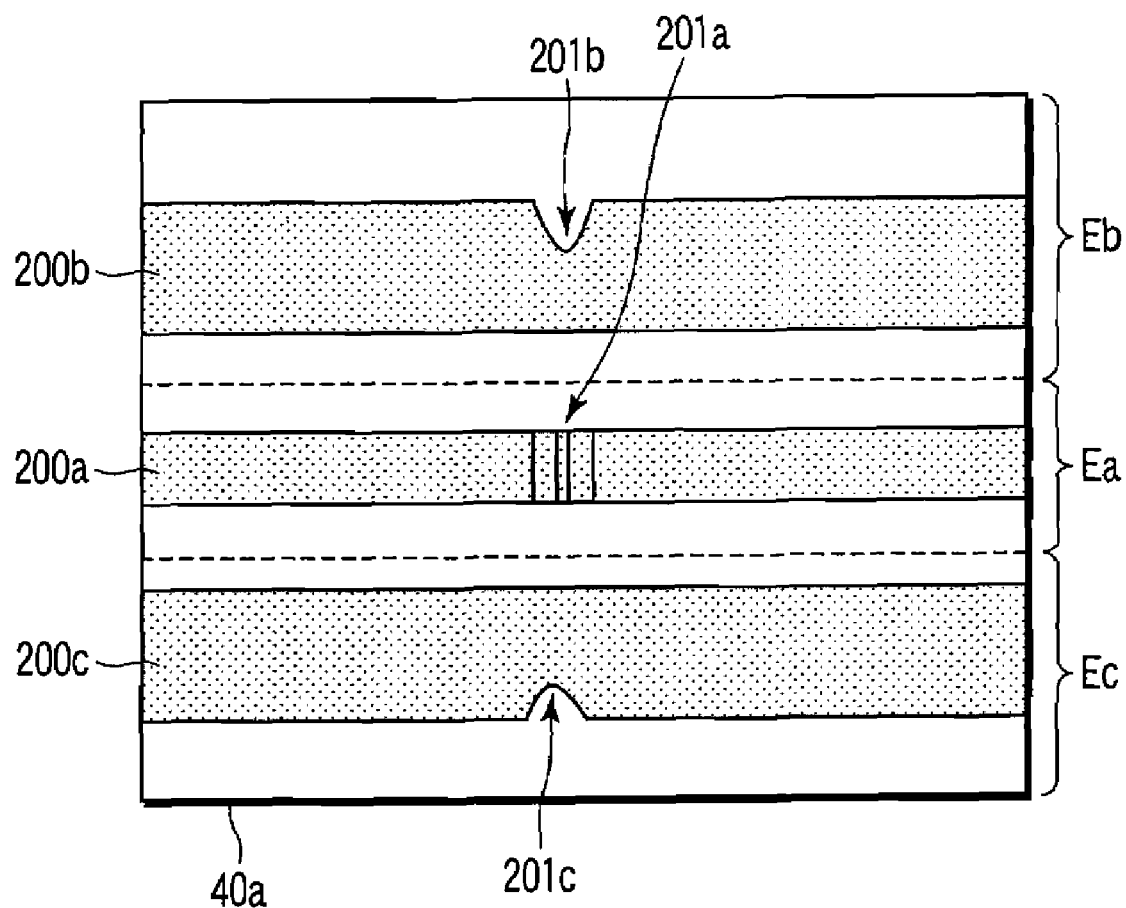
F I G. 5

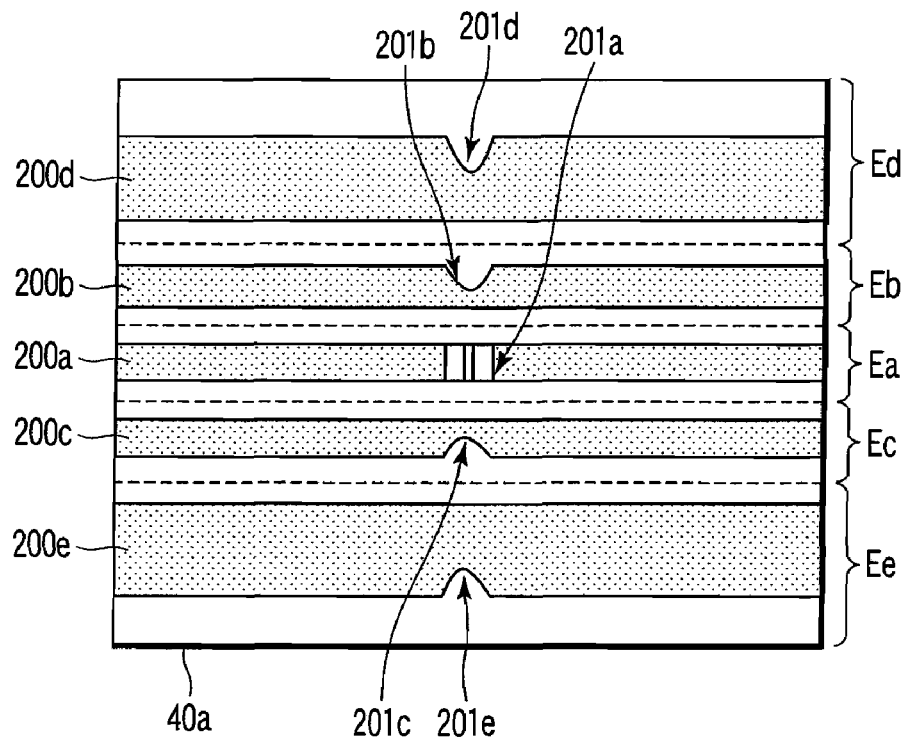
F I G. 7

SURFACE INSPECTION APPARATUS AND SURFACE INSPECTION METHOD

CROSS-REFERENCE TO RELATED APPLICATIONS

This is a Continuation Application of PCT Application No. PCT/JP2005/021997, filed Nov. 30, 2005, which was published under PCT Article 21(2) in Japanese.

This application is based upon and claims the benefit of priority from prior Japanese Patent Application No. 2004-345141, filed Nov. 30, 2004, the entire contents of which are incorporated herein by reference.

BACKGROUND OF THE INVENTION

1. Field of the Invention

The present invention relates to a surface inspection apparatus and a surface inspection method, which picks up images of a plurality of surfaces formed on a peripheral edge portion of a plate-like object, such as a silicon wafer, so that images of the plurality of surfaces can be obtained.

2. Description of the Related Art

In general, a peripheral edge portion of a plate-like object, i.e., a silicon wafer, includes a edge portions. The edge portions are formed between the circumferential surface and upper and lower plate surfaces of the silicon wafer. The edge portions are chamfered, because they are liable to be damaged due to external force applied thereto. Thus, the circumferential surface, and a first tapered surface and a second tapered surface formed by chamfering, exist in the peripheral edge portion of the silicon wafer.

If there is any defect, such as a nick, a crack, a small projection, or adhesion of particles, in the three surfaces formed in the peripheral edge portion of the plate-like object, a critical problem may arise in the silicon wafer. To avoid this, the chamfered silicon wafer is subjected to inspection whether there is any defect, such as a nick, a crack, a small projection, or adhesion of particles, in the three surfaces formed in the peripheral edge portion.

Conventionally, to inspect the peripheral edge portion of a silicon wafer, a surface inspection apparatus has been proposed, which picks up images of a plurality of surfaces of the peripheral edge portion, so that images of the plurality of surfaces can be obtained. Such conventional art is disclosed in, for example, Patent Documents 1 or 2 indicated below.

More specifically, the conventional surface inspection has first to third CCD cameras 10a, 10b and 10c as image pickup portions, as shown in FIG. 8. The peripheral edge portion of a disc-shaped silicon wafer 100 to be inspected includes the three surfaces of a circumferential surface 101a, an upper tapered surface 101b formed by chamfering the upper surface edge of the silicon wafer 100, and a lower tapered surface 101c formed by chamfering the lower surface edge of the silicon wafer 100.

The first CCD camera 10a is located in a position facing the circumferential surface 101a of the peripheral edge portion. The second CCD camera 10b is located in a position facing the upper tapered surface 101b. The third CCD camera 10c is located in a position facing the lower tapered surface 101c.

In this state, the silicon wafer 100 is rotated about a center axis (not shown), so that the first to third CCD cameras 10a, 10b and 10c independently pick up images of the circumferential surface 101a, the upper tapered surface 101b and the lower tapered surface 101c of the peripheral edge portion of the silicon wafer 100.

As a result, the surface inspection apparatus separately obtains an image corresponding to the circumferential surface 101a based on an image signal output from the first CCD camera 10a, an image corresponding to the upper tapered surface 101b based on an image signal output from the second CCD camera 10b, and an image corresponding to the lower tapered surface 101c based on an image signal output from the third CCD camera 10c.

These images are displayed in, for example, a monitor device. The inspector inspects whether there is any defect, such as a crack or adhesion of particles, in the peripheral edge portion based on the images corresponding to the circumferential surface 101a, the upper tapered surface 101b and the lower tapered surface 101c of the peripheral edge portion of the silicon wafer 100 displayed on the monitor device.

Patent Document 1: Jpn. Pat. Appln. KOKAI Publication No. 2003-139523

Patent Document 2: Jpn. Pat. Appln. KOKAI Publication No. 2003-243465

BRIEF SUMMARY OF THE INVENTION

[Problem to be Solved by the Invention]

However, in the conventional surface inspection apparatus as described above, the first to third CCD cameras 10a, 10b and 10c respectively pick up independent images of a plurality of surfaces formed on the peripheral edge portion of the silicon wafer, that is, the circumferential surface 101a, the upper tapered surface 101b and the lower tapered surface 101c, so that images of the respective surfaces are independently obtained.

Therefore, because of the three CCD cameras 10a, 10b and 10c, the apparatus itself is upsized and the cost involved is increased. Moreover, since it is necessary to synchronize the images of three screens, which are independently obtained from the first to third CCD cameras 10a, 10b and 10c, the image processing is complicated.

The present invention has been made to solve the problems of the conventional art described above. It provides a surface inspection apparatus and a surface inspection method, which reduces the cost and size of the apparatus, and can make the image processing easier.

The present invention provides a surface inspection apparatus which inspects a plurality of surfaces formed in a peripheral edge portion of a plate-like object, the apparatus comprising:

a photographing mechanism, which photographs the peripheral edge portion of the plate-like object having a plurality of surfaces; and an image processing device, which processes an image obtained by the photographing mechanism, the photographing mechanism including an optical system which guides images of the plurality of surfaces of the plate-like object in one direction, and a camera unit having an image pickup surface, on which the images of the plurality of surfaces guided by the optical system in the one direction are formed.

The present invention provides a surface inspection method for inspecting a plurality of surfaces formed in a peripheral edge portion of a plate-like object, the method comprising:

guiding images of a plurality of surfaces formed in the peripheral edge portion of the plate-like object in one direction;

forming the images of the plurality of surfaces guided in the one direction on an image pickup surface of a camera unit; and processing the images of the plurality of surfaces formed on the image pickup surface of the camera unit.

[Advantage of the Invention]

According to the surface inspection apparatus and surface inspection method of the present invention, a single camera unit can obtain images corresponding to a plurality of surfaces formed in the peripheral edge portion of a plate-like object to be inspected. Therefore, the apparatus can be cost-reduced and downsized.

Moreover, since images of a plurality of surfaces in the peripheral edge portion of a plate-like object are formed on an image pickup surface of the single camera unit, the images of the plurality of surfaces formed on the image pickup surface can be collectively processed. Therefore, the images can be processed easily.

BRIEF DESCRIPTION OF THE SEVERAL VIEWS OF THE DRAWING

FIG. 5 is a diagram showing an example of a displayed image obtained when a peripheral edge portion of the silicon wafer with a notch shown in FIG. 4 is photographed;

FIG. 7 is a diagram showing an example of a displayed image obtained when a peripheral edge portion of the silicon wafer with a notch is photographed by means of the photographing mechanism shown in FIG. 6.

DETAILED DESCRIPTION OF THE INVENTION

An embodiment of the present invention will now be described with reference to the drawings.

Figure 1:
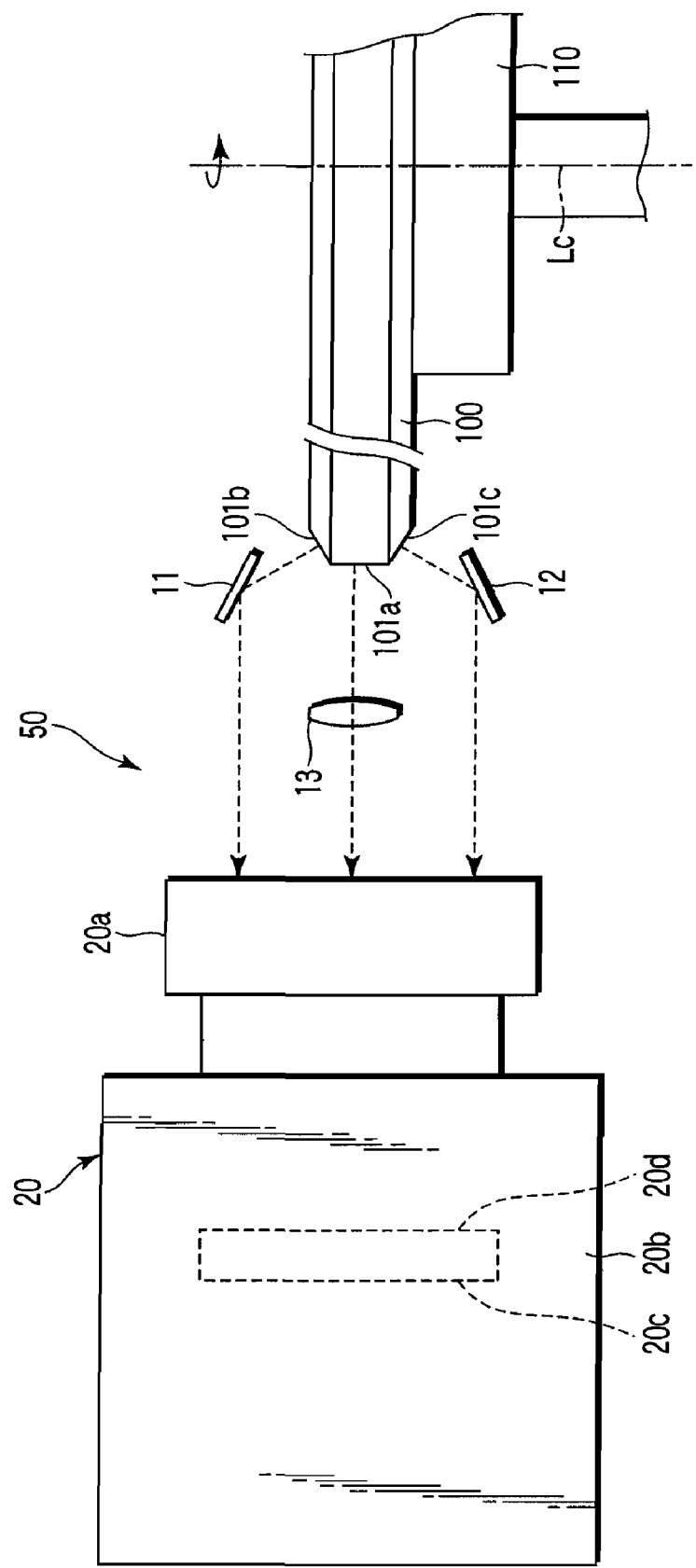
FIG. 1 is a diagram showing a configuration of a photographing mechanism of a surface inspection apparatus according to an embodiment of the present invention.

A image pickup mechanism 50 of a surface inspection apparatus according to an embodiment of the present invention is configured as shown in FIG. 1. The surface inspection apparatus inspects a plate-like silicon wafer 100, and is capable of detecting defects in a peripheral edge portion thereof, such as a crack or adhesion of particles.

Referring to FIG. 1, the silicon wafer 100 is set on a turntable 110, and rotated about a central axis Lc in accordance with the rotation of the turntable 110. The peripheral edge portion of the silicon wafer 100 has a circumferential surface 101a; a first tapered surface, namely, an upper tapered surface 101b, formed by chamfering a first edge portion made by the circumferential surface 101a and an upper surface of the silicon wafer, which is opposite to a lower surface thereof facing the turntable 110; and a second tapered surface, namely, a lower tapered surface 101c, formed by chamfering a second edge portion made by the circumferential surface 101a and the lower surface facing the turntable 110.

A first guide mirror 11 is arranged near the upper tapered surface 101b in the peripheral edge portion of the silicon wafer 100. A second guide mirror 12 is arranged near the lower tapered surface 101c. The inclinations of the first guide mirror 11 and the second guide mirror 12 are set such that an image of the upper tapered surface 101b reflected by the first guide mirror 11 and an image of the lower tapered surface 101c reflected by the second guide mirror 12 are guided in parallel and in the same direction.

A camera unit 20 has a camera lens 20a and a camera body 20b. The camera body 20b has, for example, a CCD line sensor 20c, as an image pickup element. An image guided through the camera lens 20a is formed on an image pickup surface 20d of the CCD line sensor 20c. The camera unit 20 has a view range covering the peripheral edge portion of the silicon wafer 100. It is located in a position where the image of the upper tapered surface 101b and the image of the lower tapered surface 101c, guided by the first guide mirror 11 and the second guide mirror 12, are formed on the image pickup surface 20d in a focused condition, that is, an in-focus position.

Further, the positional relationship among the upper tapered surface 101b, the first guide mirror 11 and the camera unit 20 and the positional relationship among the lower tapered surface 101c, the second guide mirror 12 and the camera unit 20 are the same. Therefore, an image of the upper tapered surface 101b and an image of the lower tapered surface 101c are simultaneously formed on the image pickup surface 20d in a focused condition, as described above.

An image of the circumferential surface 101a of the silicon wafer 100 is formed on the image pickup surface 20d in the camera body 20b via the camera lens 20a of the camera unit 20. In this case, the lengths of the optical paths respectively from the upper tapered surface 101b and the lower tapered surface 101c to the camera unit 20 via the first guide mirror 11 and the second guide mirror 12 are different from the length of the optical path from the circumferential surface 101a to the camera unit 20. In this state, therefore, the image of the circumferential surface 101a is not formed on the image pickup surface 20d in the camera body 20b in a focused condition. Therefore, a compensating lens 13 comprising a convex lens is interposed between the circumferential surface 101a of the silicon wafer 100 and the camera unit 20.

The compensating lens 13 forms a virtual image of the circumferential surface 101a of the silicon wafer 100. As a result, the length of an optical path from the virtual image forming position to the camera unit 20 coincides with the lengths of the optical paths respectively from the upper tapered surface 101b and the lower tapered surface 101c to the camera unit 20 via the first guide mirror 11 and the second guide mirror 12. Thus, the image of the circumferential surface 101a of the silicon wafer 100 is formed on the image pickup surface 20d in the camera body 20b in a focused condition via the compensating lens 13 and the camera lens 20a.

As described above, the images of the circumferential surface 101a, the upper tapered surface 101b and the lower tapered surface 101c of the peripheral edge portion are guided to form on the image pickup surface 20d of the camera unit 20 in a focused condition by means of the first guide mirror 11, the second guide mirror 12 and the compensating lens 13 as the optical system interposed between the camera unit 20 and the peripheral edge portion of the silicon wafer 100.

The compensating lens 13 may not be interposed between the camera unit 20 and the circumferential surface 101a of the silicon wafer 100. In this case, the camera unit 20 may be arranged in a position where the image of the circumferential surface 101a is formed on the image pickup surface 20d in a focused condition by adjusting the focal position of the camera lens 20a.

A compensating lens 13 comprising a concave lens is arranged in each of an optical path between the upper tapered surface 101b and the camera unit 20 and an optical path between the lower tapered surface 101c and the camera unit 20. With this structure also, the images of the circumferential surface 101a, the upper tapered surface 101b and the lower tapered surface 101c of the silicon wafer 100 can be formed on the image pickup surface 20d of the camera unit 20 in a focused condition.

The image formation on the image pickup surface 20d in a focused condition includes not only a case where an image (real image or virtual image) photographed by the camera unit 20 coincides with the focal position of the camera lens 20a but also a case where the image is formed in a range of the depth of focus of the camera lens 20a.

The surface inspection apparatus is further provided with an illumination device (not shown), which illuminates the peripheral edge portion of the silicon wafer 100. The illumination device may be, for example, a C-shaped light source used in the apparatuses disclosed in Jpn. Pat. Appln. KOKAI Publication No. 2003-139523 and Jpn. Pat. Appln. KOKAI Publication No. 2003-243465.

Figure 2:
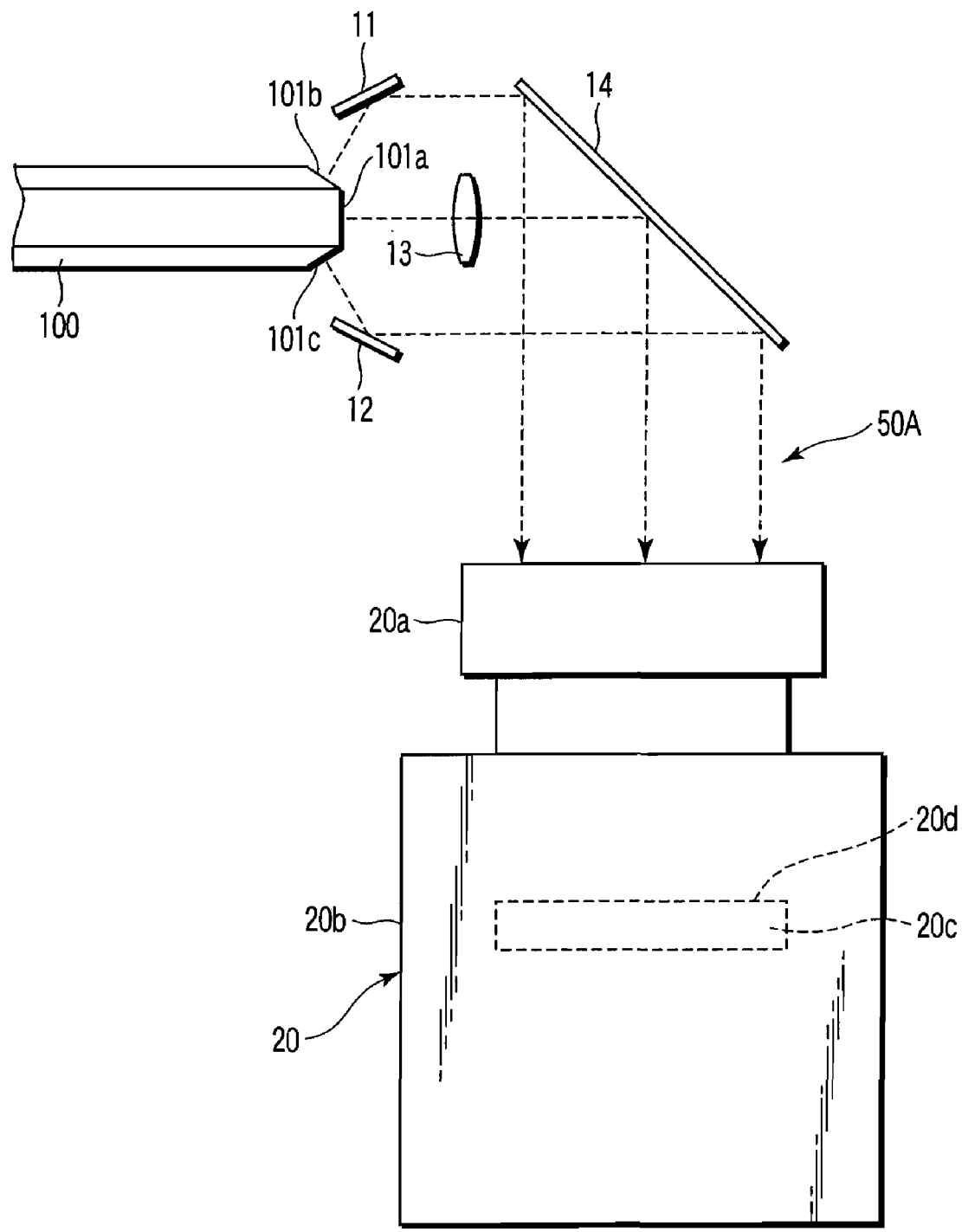
FIG. 2 is a diagram showing another configuration of the photographing mechanism of the surface inspection apparatus according to the embodiment of the present invention.

The image pickup mechanism of the surface inspection apparatus may be configured as shown in FIG. 2.

The image pickup mechanism 50A in this case comprises a direction changing mirror 14 constituting an optical system arranged between the camera unit 20 and the peripheral edge portion of the silicon wafer 100. The direction changing mirror 14 changes about 90° the direction of reflecting an image of the circumferential surface 101a of the silicon wafer 100 guided via the compensating lens 13, an image of the upper tapered surface 101b guided via the first guide mirror 11 and an image of the lower tapered surface 101c guided via the second guide mirror 12. The camera unit 20 is arranged such that the respective images reflected by the direction changing mirror 14 are formed on the image pickup surface 20d of the CCD line sensor 20c in the camera body 20b.

With the arrangement of the direction changing mirror 14, the camera unit 20, which has been arranged to face the peripheral edge portion of the silicon wafer 100 to be inspected (see FIG. 1), can be positioned sideways under the silicon wafer 100.

Figure 3:
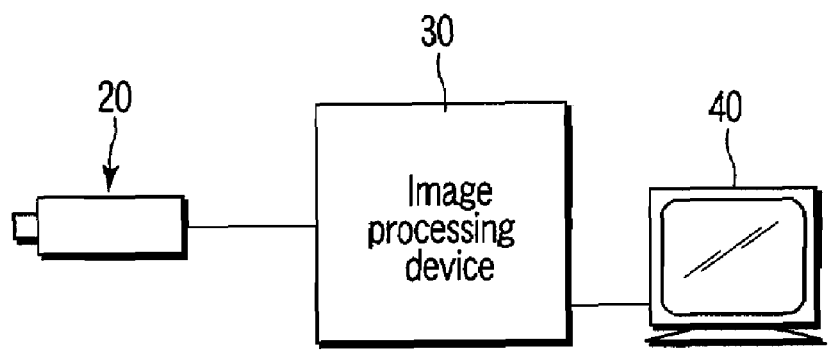
FIG. 3 is a diagram showing a basic configuration of the surface inspection apparatus according to the embodiment of the present invention.

FIG. 3 shows a basic configuration of the surface inspection apparatus including the image pickup mechanism 50 or 50A as described above. To be specific, the surface inspection apparatus comprises a camera unit 20 that is located in a predetermined position where the peripheral edge portion of the silicon wafer 100 is covered in the view range, an image processing device 30 and a monitor device 40. The camera unit 20 transmits image signals corresponding to three images of the circumferential surface 101a, the upper tapered surface 101b and the lower tapered surface 101c of the silicon wafer 100, which is rotated by the turntable 110, sequentially to the image processing device 30.

The image processing device 30 sequentially fetches image signals from the camera unit 20. Based on the image signals, it expands image data indicative of the images photographed by the camera unit 20 on an image memory for one screen. Further, the image processing device 30 sequentially outputs the image data for one screen expanded on the image memory to the monitor device 40. As a result, the image data for one screen is displayed on the monitor device 40.

As described before, the three images of the circumferential surface 101a, the upper tapered surface 101b and the lower tapered surface 101c of the silicon wafer 100 are formed on the image pickup surface 20d of the camera unit 20. Accordingly, the image for one screen based on the image signals corresponding to the three images includes the three images clearly.

Figure 4:
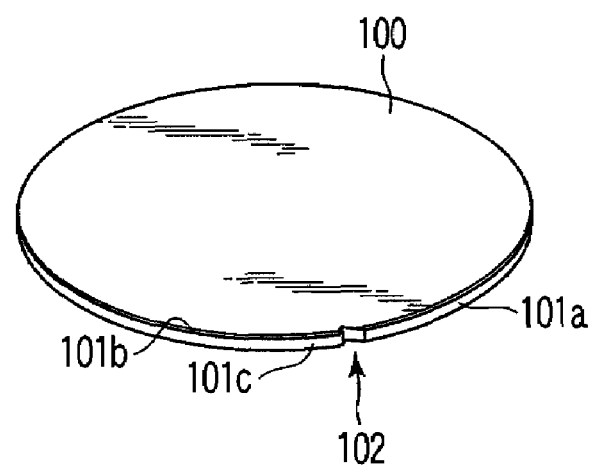
FIG. 4 is a diagram showing a silicon wafer to be photographed.

Therefore, for example, in the case where a notch 102 is formed in the peripheral edge portion of the silicon wafer 100 as shown in FIG. 4, when the notch portion 102 falls in the view range of the camera unit 20, an image as shown in FIG. 5 is fetched and displayed on the monitor device 40.

Referring to FIG. 5, the monitor device 40 displays on a screen 40a a view image portion Ea corresponding to the circumferential portion 101a of the silicon wafer 100, a view image portion Eb corresponding to the upper tapered surface 101b and a view image portion Ec corresponding to the lower tapered surface 101c, which sandwich the portion Ea.

A circumferential surface image 200a including the notch portion 201a appears in the view image portion Ea corresponding to the circumferential surface portion 101a. An upper tapered surface image 200b including the notch portion 201b appears in the view image portion Eb corresponding to the upper tapered surface portion 101b. A lower tapered surface image 200c including the notch portion 201c appears in the view image portion Ec corresponding to the lower tapered surface portion 101c.

The circumferential surface image 200a, the upper tapered surface image 200b and the lower tapered surface image 200c are originally included in one screen. Therefore, without synchronizing these images, the positions of the notch portion 201a of the circumferential surface image 200a, the notch portion 201b of the upper tapered surface image 200b and the notch portion 201c of the lower tapered surface image 200c in the horizontal direction are the same.

The inspector can visually inspect whether there is any defect, such as a nick, a crack, a small projection, or adhesion of particles, in the circumferential surface 101a, the upper tapered surface 101b and the lower tapered surface 101c of the peripheral edge portion based on the circumferential surface image 200a, the upper tapered surface image 200b and the lower tapered surface image 200c, which appear on the screen 40a of the monitor device 40 as an image for one screen.

According to the surface inspection apparatus as described above, the peripheral edge portion of the silicon wafer 100 is photographed by the single camera unit 20. As a result, the monitor device 40 can display a clear image for one screen including the circumferential surface image 200a, the upper tapered surface image 200b and the lower tapered surface image 200c respectively corresponding to the circumferential surface 101a, the upper tapered surface 101b and the lower tapered surface 101c of the peripheral edge portion. Thus, since it is unnecessary to use a plurality of cameras to independently photograph the respective surfaces, the apparatus can be cost-reduced and downsized.

The image processing device 30 processes image data corresponding to the images of the circumferential surface 101a, the upper tapered surface 101b and the lower tapered surface 101c, not individually but as a unit of image data for one screen. Therefore, the amount of images to be processed can be reduced. In addition, even if the silicon wafer 100 to be inspected is rotated, the images corresponding to the respective surfaces need not be synchronized when displayed. Consequently, the processing in the image processing device 30 is relatively simple.

Figure 6:
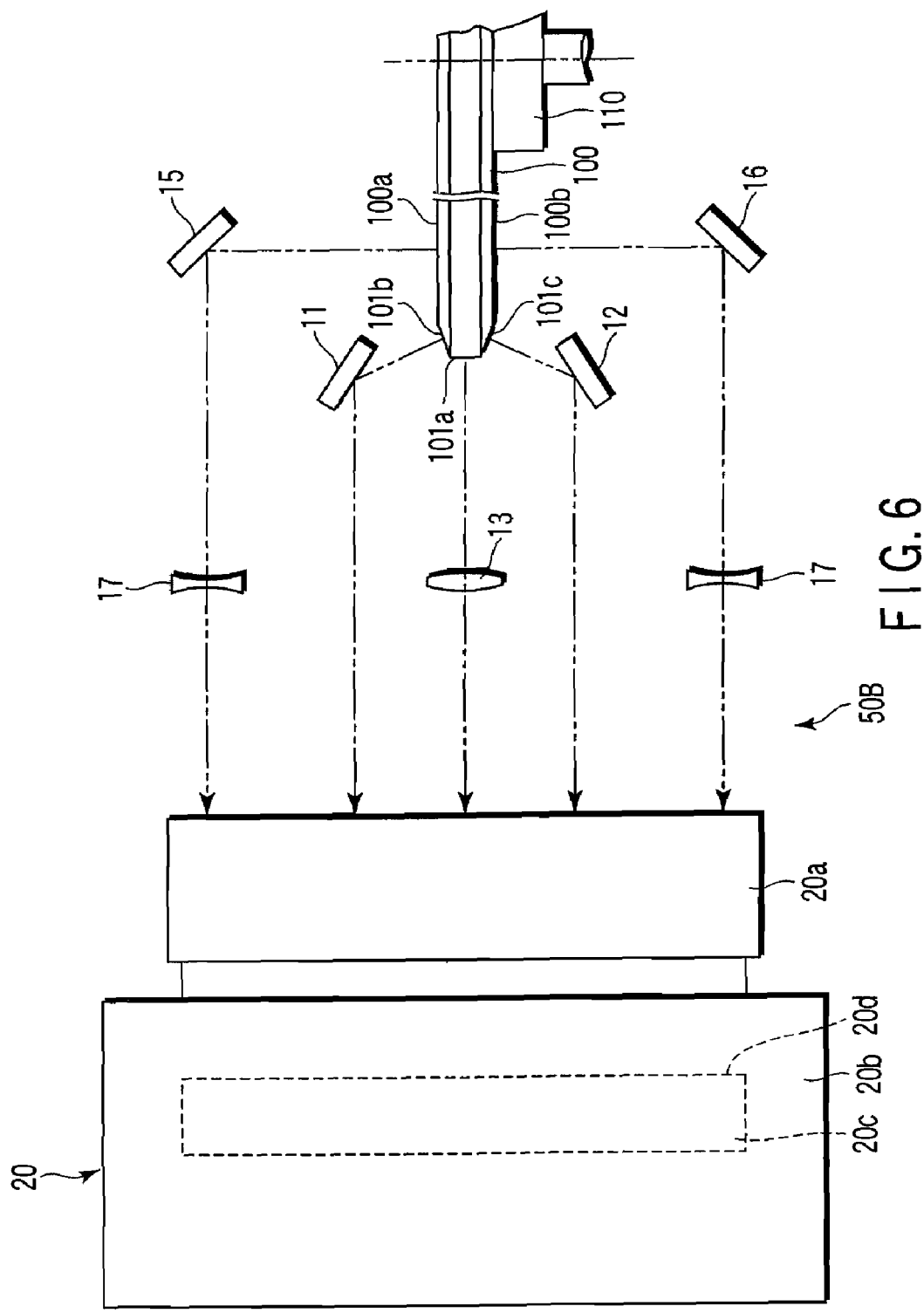
FIG. 6 is a diagram showing still another configuration of the photographing mechanism of the surface inspection apparatus according to the embodiment of the present invention.
Figure 8:
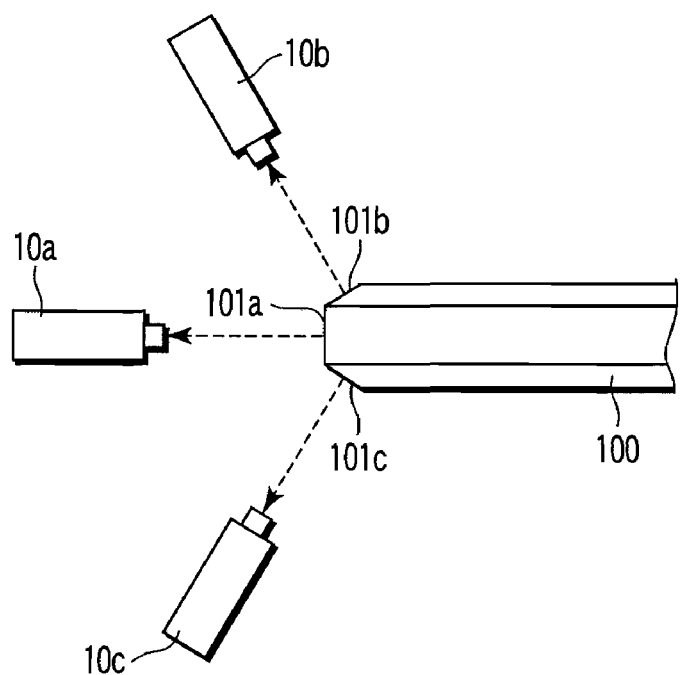
FIG. 8 is a diagram showing a configuration of a photographing mechanism of a conventional surface inspection apparatus.

FIG. 6 shows still another embodiment of the surface inspection apparatus. The same parts as those shown in FIG. 1 are identified by the same symbols, and detailed descriptions thereof will be omitted.

The image pickup mechanism 50 shown in FIG. 1 picks up images of the circumferential surface 101a, the upper tapered surface 101b and the lower tapered surface 101c of the silicon wafer 100. On the other hand, the image pickup mechanism 50B shown in FIG. 6 picks up images of a peripheral edge portion upper surface 100a and a peripheral edge portion lower surface 100b of the silicon wafer 100 on the image pickup surface 20d of the camera body 20b via the camera lens 20a of the camera unit 20, in addition to the images of the three surfaces described above.

More specifically, in the image pickup mechanism 50B, a third guide mirror 15 is arranged near the peripheral edge portion upper surface 100a of the silicon wafer 100, and a fourth guide mirror 16 is arranged near the peripheral edge portion lower surface 100b. The inclinations of the third guide mirror 15 and the fourth guide mirror 16 are set such that an image of the peripheral edge portion upper surface 100a reflected by the third guide mirror 15 and an image of the peripheral edge portion lower surface 100b reflected by the fourth guide mirror 16 are guided in parallel to and in the same direction as those of the image of the upper tapered surface 101b reflected by the first guide mirror 11 and the image of the lower tapered surface 101c reflected by the second guide mirror 12.

An image of the peripheral edge portion upper surface 100a and an image of the peripheral edge portion lower surface 100b of the silicon wafer 100 are formed on the image pickup surface 20d in the camera body 20b via the camera lens 20a of the camera unit 20. In this case, the lengths of the optical paths respectively from the upper tapered surface 101b and the lower tapered surface 101c to the camera unit 20 via the first guide mirror 11 and the second guide mirror 12 are different from the lengths of the optical paths respectively from the peripheral edge portion upper surface 100a and the peripheral edge portion lower surface 100b to the camera unit 20. In this state, therefore, the image of the peripheral edge portion upper surface 100a and the image of the peripheral edge portion lower surface 100b are not formed on the image pickup surface 20d in the camera body 20b in a focused condition.

Therefore, compensating lenses 17, each comprising a concave lens, are respectively interposed between the peripheral edge portion upper surface 100a of the silicon wafer 100 and the camera unit 20, and between the peripheral edge portion lower surface 100b and the camera unit 20.

With the arrangement of the compensating lenses 17, the lengths of both optical paths can be optically aligned. Therefore, when the images of the peripheral edge portion upper surface 100a and the peripheral edge portion lower surface 100b of the silicon wafer are guided into the camera body 20b via the compensating lenses 17 and the camera lens 20a, these images are formed on the image pickup surface 20d of the CCD line sensor 20c in a focused condition.

Thus, in this embodiment, the five images of the circumferential surface 101a, the upper tapered surface 101b, the lower tapered surface 101c, the peripheral edge portion upper surface 100a, and the peripheral edge portion lower surface 100b are formed on the image pickup surface 20d of the single camera unit 20 in a focused condition by the first to fourth guide mirrors 11, 12, 15 and 16 and compensating lenses 13 and 17.

The camera unit 20 transmits image signals corresponding to five images of the silicon wafer 100, which is rotated by the turntable 110, sequentially to the image processing device 30 shown in FIG. 3. The image processing device 30 sequentially fetches image signals from the camera unit 20. Based on the image signals, it expands image data indicative of the images photographed by the camera unit 20 on an image memory for one screen. Further, the image processing device 30 sequentially outputs the image data for one screen expanded on the image memory to the monitor device 40.

FIG. 7 shows an image displayed on the screen 40a of the monitor device 40, when the part of the silicon wafer 100, which corresponds to that shown in FIG. 5, was photographed by means of the image pickup mechanism 50B.

FIG. 7 differs from FIG. 5 in that a view image portion Ed corresponding to the peripheral edge portion upper surface 100a of the silicon wafer 100 and a view image portion Ee corresponding to the peripheral edge portion lower surface 100b are displayed respectively in the uppermost position and the lowermost position in the screen 40a of the monitor device 40. A peripheral edge portion upper surface image 200d including the notch portion 201d appears in the view image portion Ed corresponding to the peripheral edge portion upper surface 100a, and a peripheral edge portion lower surface image 200e including the notch portion 201e appears in the view image portion Ee corresponding to the peripheral edge portion lower surface 100b.

According to this embodiment, one screen includes the five images of the circumferential surface image 200a, the upper tapered surface image 200b, the lower tapered surface image 200c, the peripheral edge portion upper surface image 200d and the peripheral edge portion lower surface image 200e.

Therefore, without synchronizing these five images, the positions in the horizontal direction of the notch portion 201a of the circumferential surface image 200a, the notch portion 201b of the upper tapered surface image 200b, the notch portion 201c of the lower tapered surface image 200c, the notch portion 201d of the peripheral edge portion upper surface image 200d and the notch portion 201e of the peripheral edge portion lower surface image 200e are the same.

As a result, the inspector can visually inspect whether there is any defect, such as a nick, a crack, a small projection, or adhesion of particles, in the circumferential surface 101a, the upper tapered surface 101b, the lower tapered surface 101c, the peripheral edge portion upper surface 100a and the peripheral edge portion lower surface 100b of the silicon wafer 100 based on the screen 40a of the monitor device 40.

The optical system provided between the camera unit 20 and the peripheral edge portion of the silicon wafer 100 to be inspected is not limited to the configurations shown in FIGS. 1, 2 and 6. Any configuration can be used as far as the images of a plurality of surfaces constituting the peripheral edge portion can be guided to the camera unit 20 and formed on the image pickup surface 20d of the CCD line sensor 20c.

The image processing device 30 not only displays images on the monitor device 40 in accordance with image signals from the camera unit 20, but may further carry out predetermined image analysis, thereby automatically determining the presence or absence of a defect, the number of defects, the classification thereof, etc.

The surface inspection apparatus and the surface inspection method of the present invention allow cost reduction and downsizing of the apparatus, and make the image processing easier. The present invention is particularly useful as a surface inspection apparatus and a surface inspection method to inspect a plurality of surfaces formed on a peripheral edge portion of a silicon wafer or the like.

According to the surface inspection apparatus and the surface inspection method of the present invention, images corresponding to a plurality of surfaces in a peripheral edge portion of a plate-like object to be inspected are obtained by a single camera unit. Therefore, the cost and size of the apparatus can be reduced.

Further, images of a plurality of surfaces in a peripheral edge portion of a plate-like object to be inspected are formed on an image pickup surface of the single camera unit, and images corresponding to the plurality of images of the plurality of surfaces formed on the image pickup surface can be collectively processed. Therefore, the image processing can also be easier.

What is claimed is:

1. A surface inspection apparatus which inspects a plurality of surfaces formed in a peripheral edge portion of a plate-like object, the apparatus comprising:
    a photographing mechanism, which photographs the peripheral edge portion of the plate-like object having a plurality of surfaces; and
    an image processing device, which processes an image obtained by the photographing mechanism;
    the photographing mechanism including an optical system which guides images of the plurality of surfaces of the plate-like object in one direction, and a camera unit having an image pickup surface, on which the images of the plurality of surfaces guided by the optical system in the one direction are formed;
    wherein the peripheral edge portion of the plate-like object includes a circumferential surface of the plate-like object, a first tapered surface formed by chamfering a first edge portion made by the circumferential surface and a first surface of the plate-like object, and a second tapered surface formed by chamfering a second edge portion made by the circumferential surface and a second surface of the plate-like object; and
    the optical system includes a first guide mirror which reflects an image of the first tapered surface and guides the image to the camera unit, a second guide mirror which reflects an image of the second tapered surface and guides the image to the camera unit, and a compensating lens which is mounted between the camera unit and the circumferential surface and forms the image of the circumferential surface on the image pickup surface of the camera unit.

2. The surface inspection apparatus according to claim 1, wherein the optical system includes a direction changing mirror, which reflects the images guided through the first guide mirror, the second guide mirror and the compensating lens in a predetermined direction; and
    the images reflected by the direction changing mirrors are formed on the image pickup surface of the camera unit.

3. The surface inspection apparatus according to claim 1, further comprising a turntable on which the plate-like object is mounted, and which rotates the plate-like object.

4. A surface inspection method for inspecting a circumferential surface of a plate-like object, a first tapered surface formed by chamfering a first edge portion made by the circumferential surface and a first surface of the date-like object, and a second tapered surface formed by chamfering a second edge portion made by the circumferential surface and a second surface of the plate-like object, the method comprising:
    forming an image of the first tapered surface on an image pickup surface of a camera unit by reflecting the image with a first guide mirror
    forming an image of the second tapered surface on the image pickup surface of the camera unit by reflecting the image with a second guide mirror; and
    forming an image of the circumferential surface on the image pickup surface of the camera unit by compensating the image by a compensating lens mounted between the camera unit and the circumferential surface.

5. The surface inspection method according to claim 4, wherein the plate-like object is rotated, when the images of the circumferential surface, the first tapered surface, and the second tapered surface are formed on the image pickup surface of the camera unit.

6. The surface inspection apparatus according to claim 1, further comprising:
    a third guide mirror which reflects an image of a peripheral edge portion upper surface of the plate-like object and guides the image to the camera unit,
    a fourth guide mirror which reflects an image of a peripheral edge portion lower surface of the plate-like object and guides the image to the camera unit, and
    a compensating lens which is mounted between the camera unit and the peripheral edge portion upper surface of the plate-like object, and between the camera unit and the peripheral edge portion lower surface of the plate-like object, respectively, and forms the images of the peripheral edge portion upper and lower surfaces on the image pickup surface of the camera unit.

* * * * *